United States Patent
Tanimoto

(10) Patent No.: US 6,781,013 B2
(45) Date of Patent: Aug. 24, 2004

(54) PROCESS FOR PRODUCING ACROLEIN AND ACRYLIC ACID

(75) Inventor: Michio Tanimoto, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 95 days.

(21) Appl. No.: 09/778,747

(22) Filed: Feb. 8, 2001

(65) Prior Publication Data

US 2001/0021789 A1 Sep. 13, 2001

(30) Foreign Application Priority Data

Feb. 16, 2000 (JP) ........................ 2000-037550

(51) Int. Cl.$^7$ ............... C07C 51/16; C07C 51/42
(52) U.S. Cl. .......... 562/532; 562/534; 562/536; 562/544; 562/546; 562/548; 562/600
(58) Field of Search .............. 562/532, 534, 562/535, 536, 544, 546, 548, 600

(56) References Cited

U.S. PATENT DOCUMENTS

| | | | | |
|---|---|---|---|---|
| 4,259,211 A | * | 3/1981 | Krabetz et al. | ............ 252/443 |
| 4,341,900 A | * | 7/1982 | Ishii et al. | ............ 562/532 |
| 4,365,087 A | * | 12/1982 | Kadowaki et al. | ........... 562/534 |
| 4,435,598 A | * | 3/1984 | Hinnenkamp | ............... 562/546 |
| 4,837,360 A | | 6/1989 | Kadowaki | |
| 5,264,625 A | * | 11/1993 | Hammon et al. | ............ 562/532 |
| 6,028,220 A | * | 2/2000 | Wada et al. | ................ 562/546 |

FOREIGN PATENT DOCUMENTS

| | | |
|---|---|---|
| EP | 0450596 | 10/1991 |
| EP | 0900774 | 3/1999 |
| EP | 1055662 | 11/2000 |
| EP | 1074538 | 2/2001 |
| JP | 8003093 | 1/1996 |
| WO | WO98/24746 | * 11/1998 |

* cited by examiner

*Primary Examiner*—Ba K. Trinh
*Assistant Examiner*—Taylor V Oh
(74) *Attorney, Agent, or Firm*—Sherman & Shalloway

(57) ABSTRACT

A process is provided which can effectively inhibit occurrence of hot spots in reaction zones or heat accumulation at the hot spots, in the occasion of producing acrolein and acrylic acid through vapor phase oxidation of propylene in the presence of a catalyst using a fixed bed shell-and-tube reactor, said catalyst having a composition represented by a general formula (1):

$$Mo_a W_b Bi_c Fe_d A_e B_f C_g D_h E_i O_x$$

(wherein A is at least an element selected from Co and Ni; B is at least an element selected from P, Te, As, B, Sb, Sn, Ce, Nb, Pb, Cr, Mn and Zn; C is alkali metal element; D is alkaline earth metal element; E is at least an element selected from Si, Al, Ti and Zr; and O is oxygen; a, b, c, d, e, f, g, h, i and x denote the atomic numbers of Mo, W, Bi, Fe, A, B, C, D, E and O, respectively, and where a is 12, b is 0–5, c is 0.1–10, d is 0.1–10, e is 1–20, f is 0–5, g is 0.001–3, h is 0–3, i is 0–30, and x is a numerical value which is determined depending on the extent of oxidation of each of the elements).

Said process is characterized by preparing plural kinds of catalysts having the above composition but differing from each other in (α) occupying volume, (β) calcining temperature and/or (γ) kind and/or amount of alkali metal element, and filling the reaction zones provided by dividing the catalyst layer in each of the reaction tubes in the reactor into at least two layers in the axial direction of the tube, sequentially with said plural kinds of catalysts in such a manner that the catalytic activity increases from the starting gas inlet side toward the outlet side.

4 Claims, No Drawings

PROCESS FOR PRODUCING ACROLEIN AND ACRYLIC ACID

TECHNICAL FIELD TO WHICH THE INVENTION BELONGS

This invention relates to a process for producing acrolein and acrylic acid. More specifically, the invention relates to a process for producing acrolein and acrylic acid by oxidizing propylene at vapor phase in the presence of a molybdenum-bismuth-containing oxidation catalyst.

Prior Art

It has been industrially widely practiced to oxidize propylene at vapor phase with molecular oxygen or molecular oxygen-containing gas in the presence of a molybdenum-bismuth-containing oxidation catalyst, using a fixed bed shell-and-tube reactor.

Because this vapor-phase oxidation is a highly exothermic reaction, a hot spot is apt to form in the catalyst layer in each reaction tube. Occurrence of the hot spots causes over-oxidation to reduce yield of acrolein and acrylic acid. Also the excessive heat generation at the hot spots deteriorates the catalyst, rendering it impossible to carry out the oxidation reaction over a prolonged period with stability. In particular, the problems of hot spots become more notable when the propylene concentration in the inlet gas is increased or the space velocity is raised for higher productivity. For inhibiting occurrence of hot spots, there have been a number of proposed methods.

For example, Japanese Patent Kokai (laid-open) Sho 55 (1980)-113730 discloses a method comprising preparing plural molybdenum-bismuth-containing oxidation catalysts which exhibit different activity levels, by varying the kind and/or amount of the metals (K, Rb, Cs or Tl) constituting the D-component of said catalysts and sequentially charging the reaction tubes with the plural catalysts in such a manner that the catalytic activity should increase from the starting gas inlet side toward the outlet side. According to such a method, however, the plural kinds of the catalysts exhibiting different activity levels cannot be prepared with good reproducibility because the content of the D-component is less than those of the other components. Again, although it was advocated that the method enabled to increase the propylene concentration in the starting gas, the actually used propylene concentration in the starting gas to verify the effect of the method by working examples was 8 volume % (cf. Example 7).

Japanese Patent Kokai Hei 8 (1996)-3093 describes a method of charging the reaction tubes sequentially with plural kinds of catalysts of different activity levels which are prepared by varying their calcining temperature, in such a manner as to increase the activity from the starting gas inlet side toward the outlet side. While it is possible to control the activity level by calcination according to said method, the temperature distribution inside of those ovens which are normally used for the calcination is not uniform and there is the possibility that preparation of plural kinds of catalysts of different activity levels with good reproducibility may become difficult, particularly when the catalysts are to be prepared in large amounts. Again, while the suitable propylene concentration in the starting gas according to said method is said to range 3–15 volume %, the actual concentration whose effect has been actually confirmed by working examples was 7.4 volume %.

Furthermore, Japanese Patent Kokai Hei 4 (1992)-217932 proposes a method for inhibiting occurrence of hot spots or heat accumulation at the hot spots, by preparing plural kinds of the catalysts having differing occupying volumes and filling the reaction tubes sequentially with the catalysts of less occupying volume from the starting gas inlet side toward the outlet side. According to said method, however, the occupying volumes of the catalysts are limited by the diameter of each reaction tube, and occasions will occur where filling of desired plural kinds of catalysts in the reaction tubes is difficult. This method, therefore, is not yet fully satisfactory as to inhibition of occurrence of hot spots.

OBJECT OF THE INVENTION

The object of the invention is to provide an industrially advantageous production process of acrolein and acrylic acid, which can more effectively inhibit occurrence of hot spots in the reaction zone or heat accumulation at the hot spots, compared to those prior art techniques, in particular, where the propylene concentration in starting gas is high.

MEANS TO ACHIEVE THE OBJECT

We have discovered, for achieving the above object by a production process of acrolein and acrylic acid through vapor phase catalytic oxidation of propylene in the presence of a molybdenum-bismuth-containing oxidation catalyst which is expressed by a general formula (1):

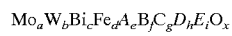

(The symbols in the formula are as defined later), that (α) occupying volume: (β) calcining temperature; and (γ) kind and/or amount of alkali metal element, of the catalyst must satisfy certain specific conditions.

Thus, according to the invention, a process for producing acrolein and acrylic acid through vapor phase catalytic oxidation of propylene with molecular oxygen or molecular oxygen-containing gas using a fixed bed shell-and-tube reactor is provided, which process comprises preparing plural kinds of catalysts which are formed of complex oxides of the composition expressed by a general formula (1):

(wherein Mo is molybdenum; W is tungsten; B is bismuth; Fe is iron; A is at least an element selected from cobalt and nickel; B is at least an element selected from phosphorus, tellurium, arsenic, boron, antimony, tin, cerium, niobium, lead, chromium, manganese and zinc; C is at least an element selected from alkali metal elements; D is at least an element selected from alkaline earth metal elements; E is at least an element selected from silicon, aluminum, titanium and zirconium; and O is oxygen: a, b, c, d, e, f, g, h, i and x denote the atomic numbers of Mo, W, Bi, Fe, A, B, C, D, E and 0, respectively, and where a is 12, b is 0–5, c is 0.1–10, d is 0.1–10, e is 1–20, f is 0–5, g is 0.001–3, h is 0–3, i is 0–30, and x is a numerical value which is determined depending on the extent of oxidation of each of the elements)

and which are different from each other in (α) occupying volume, (β) calcining temperature and/or (γ) kind and/or amount of the alkali metal element, and filling the reaction zones provided by dividing the catalyst layer in each of the reaction tubes in the fixed bed shell-and-tube reactor into at least two layers in the axial direction of the tube, sequentially with said plural kinds of catalysts in such a manner that the catalytic activity increases from the starting gas inlet side toward the outlet side.

This invention concerns an improvement in the invention which is described in the earlier cited Japanese Patent Kokai Hei 4 (1992)-217932. The improvement resides in the use of plural kinds of catalysts exhibiting different activity levels, which are obtained by varying not only the catalyst's occupying volumes but also the calcining temperatures and/or the kind and/or amount of alkali metal element therein. As the result, occurrence of hot spots or accumulation of heat at the hot spots are more effectively inhibited and the propylene concentration in the starting gas can be increased. According to the invention, furthermore, the desired plural catalysts of different activity levels can be prepared with better reproducibility than that in the conventional methods.

The level of "activity" as referred to in the present invention is evaluated by conversion of propylene.

MODE OF WORKING THE INVENTION

The molybdenum-bismuth-containing oxidation catalysts which are represented by the general formula (1) are known. For example, Japanese Patent Kokai Sho 50 (1975)-13308 and Sho 50-47915 taught the catalysts containing as essential components Mo, Bi, Fe, Sb, Ni and additionally at least one element selected from K, Rb and Cs. Japanese Patent Kokai Sho 64 (1989)-56634 taught the catalysts containing as essential components Mo, Bi, Fe and additionally at least either one of Ni and Co; Japanese Patent Publication (Kokoku) Sho 47 (1972)-42241, the catalysts whose essential components are Mo, Bi, Fe, Co, W and an alkali metal; and Patent Publication (Kokoku) Sho 56 (1981)-52013, the catalysts containing as essential components are Mo, Bi, Fe, and additionally at least one element selected from Mg, Ca, Zn, Cd and Ba. Those molybdenum-bismuth-containing oxidation catalysts according to the invention can be prepared by similar methods using similar starting materials to those of conventional art.

It is required according to the invention to prepare plural kinds of catalysts exhibiting different activity levels, which are the molybdenum-bismuth-containing oxidation catalysts having the composition as expressed by the general formula (1) and differing from each other in ($\alpha$) occupying volume, ($\beta$) calcining temperature and/or ($\gamma$) kind and/or amount of alkali metal element, as the catalysts to be filled in the plural reaction zones in the reaction tubes. The catalysts may be supported on generally used carriers such as $\alpha$-alumina, silicon carbide, pumice, silica, zirconium oxide, titanium oxide, and the like.

The term, "occupying volume", as used herein signifies the space occupied by particles of each of the catalysts, when they are filled in the reaction zones. As to catalysts differing in occupying volume and their preparation, Japanese Patent Kokai Hei 4 (1992)-217932 can be referred to. More specifically, where the catalyst particles are spherical, catalysts of differing occupying volumes can be prepared by varying diameter of the spheres. In particular, a spherical catalyst whose particle diameters are varied within a range of 3–15 mm is conveniently used. Occupying volume of columnar catalyst can be varied by changing the diameter and/or length of the columns. In particular, a columnar catalyst whose diameter and/or length is varied within a range of 3–15 mm is conveniently used. For ring-formed catalyst, its occupying volume can be varied by changing outer diameter and/or height of the rings. In particular, a ring catalyst whose outer diameter and/or height of the rings is varied within a range of 3–15 mm is conveniently used. Whereas, the inner diameter of the rings is optional because it does not influence the occupying volume. The occupying volume, diameter, length and height, etc. as referred to in the above mean the average values of catalyst particles to be filled in the reaction zones.

Shape of the catalyst to be used in the present invention is subject to no particular limitation, which may be spherical, columnar (pelletized) or ring-formed. Obviously, "spherical" catalyst is not required to be true spheres, but it is sufficient that the particles are substantially spherical. This applies also to columnar or ring-formed catalysts.

The term "calcining temperature", as used herein means the temperature of final calcination for activation, which is conducted in the course of the catalyst preparation. Final calcining temperature is that used for the calcining in air, for example after condensing and drying a slurry of starting materials, or after molding, and which normally ranges 300–650° C., preferably 400–600° C. By varying the calcining temperature within the above-specified range, catalysts differing in calcining temperature can be obtained.

The variation in the amount of alkali metal element must be done, for the obvious reason, within the range of the atomic ratio (g=0.001–3) as specified as to the general formula (1).

The vapor-phase oxidation reaction of propylene according to the invention can be carried out following any of heretofore known methods, except that plural kinds of catalysts which are molybdnum-bismuth-containing oxidation catalyst having the composition as expressed by the general formula (1) and are different from each other in ($\alpha$) occupying volume, ($\beta$) calcining temperature and/or ($\gamma$) kind and/or amount of the alkali metal element are prepared and said catalysts are sequentially filled in plural reaction zones in such a manner that the catalytic activity rises from the starting gas inlet side toward the outlet side. The reaction is performed, for example, by introducing a gaseous mixture comprising 1–15 volume % of propylene, 3–20 volume % of molecular oxygen, 0–60 volume % of steam, 20–80 volume % of an inert gas (nitrogen, carbon dioxide or the like) into the catalyst layers at a temperature of 250–450°C., under a pressure of 0.1–1 MPa and at a space velocity of 300–5,000 $h^{-1}$ (STP). The process of the present invention is particularly suitable for vapor-phase oxidation of materials of high propylene content, in which the propylene concentration in the starting gas is at least 9 vol. %, preferably at least 9.5 vol. %, inter alia, 10–15 vol. %.

EFFECT OF THE INVENTION

The catalysts used in the invention excel in reproducibility and suit for mass production. Namely, they can be mass-produced as catalysts exhibiting uniform performance.

According to the process of the invention, occurrence of hot spots or accumulation of heat at the hot spots can be effectively prevented. Consequently, acrolein and acrylic acid can be produced with high selectivity and at high yield. Furthermore, catalyst deterioration also is prevented and the catalyst can be used stably over a prolonged period.

The process according to the invention also achieves production of acrolein and acrylic acid with high selectivity at high yield, even under high load reaction conditions such as high starting material concentration and high space velocity, e.g., when the propylene concentration in the starting gas is raised as above. Thus the productivity is improved.

As above, the process of the present invention is extremely useful for industrial scale production of acrolein and acrylic acid.

EXAMPLES

Hereinafter the present invention is explained more specifically referring to working Examples, in which conversion, selectivity and one-pass yield are defined as follows:

propylene conversion (mol %)=(mol number of reacted propylene/mol number of supplied propylene)×100 selectivity (mol %)=(total mol number of formed acrolein and acrylic acid/mol number of reacted propylene)×100 one-pass yield (mol %)=(total mol number of formed acrolein and acrylic acid/mol number of supplied propylene)×100

Referential Example 1

(Preparation of Catalyst)

Into 1 L of ion-exchange water, 962 g of cobalt nitrate and 267 g of ferric nitrate were dissolved. Separately, 92 g of bismuth nitrate was dissolved in aqueous solution of nitric acid formed of 50 ml of conc. nitric acid and 200 ml of ion-exchange water. Again separately 1,000 g of ammonium paramolybdate and 64 g of ammonium paratungstate were added to 3 L of heated ion-exchange water and dissolved under stirring. Into this solution the above separately prepared two aqueous solutions were added dropwise under mixing, followed by addition of an aqueous solution obtained by dissolving 0.9 g of cesium nitrate in 50 ml of ion-exchange water, and 141 g of silica sol of 20 wt% in concentration, by the order stated. Thereafter 178 g of basic bismuth nitrate (product of Kanto Kagaku K.K.) was added, and the formed slurry was evaporated and solidified by stirring under heating, followed by further drying. The resulting solid was pulverized, molded into rings of each 6 mm in outer diameter, 2 mm in inner diameter and 6 mm in height, and calcined in an air stream at 480° C. for 8 hours to provide catalyst (1). The composition of the metal elements of this catalyst (1) (atomic ratio excluding oxygen; which is the same to all the compositions of metal elements given hereafter) was as follows:

$Mo_{12}W_{0.5}Bi_{1.7}Fe_{1.4}Co_7Cs_{0.01}Si_1$.

The occupying volume, calcining temperature and atomic ratio of alkali metal (Cs) (the value where the atomic ratio of molybdenum is set to be 12, which is same in all of the following examples) of catalyst (1) were as follows:

occupying volume: 170 mm³ calcining temperature: 480° C.

atomic ratio of Cs: 0.01.

(Oxidation Reaction)

A stainless steel reactor of 25 mm in diameter was charged with 400 ml of catalyst (1), and into which a gaseous mixture of 5 volume % of propylene, 10 volume % of oxygen, 25 volume % of steam and 60 volume % of inert gas whose chief component was nitrogen was introduced at a contact time of 2.4 seconds. The oxidation reaction was conducted under the conditions of the reaction temperature of 320° C., and the entrance pressure of 0.2 MPa. The results were as shown in Table 1.

Referential Example 2

(Preparation of Catalyst)

Catalyst (2) was prepared in the identical manner with Referential Example 1, except that the amount of cesium nitrate was changed to 1.8 g; the shape of the catalyst, to rings of each 9 mm in outer diameter, 2 mm in inner diameter and 9 mm in height; and the calcining temperature, to 490° C. The composition of the metal elements of catalyst (2) was as follows:

$Mo_{12}W_{0.5}Bi_{1.7}Fe_{1.4}Co_7Cs_{0.02}Si_1$.

The occupying volume, calcining temperature and atomic ratio of alkali metal (Cs) of catalyst (2) were as follows:

occupying volume: 573 mm³ calcining temperature: 490° C.

atomic ratio of Cs: 0.02.

(Oxidation Reaction)

Oxidation reaction of propylene was conducted under identical conditions with those used in Referential Example 1, except that catalyst (2) was used instead of catalyst (1). The results were as shown in Table 1.

Referential Example 3

(Preparation of Catalyst)

Catalyst (3) was prepared in the identical manner with Referential Example 1, except that the shape of the catalyst was changed to rings of each 9 mm in outer diameter, 2 mm in inner diameter and 9 mm in height and the calcining temperature was changed to 500° C. The composition of the metal elements of catalyst (3) was as follows:

$Mo_{12}W_{0.5}Bi_{1.7}Fe_{1.4}Co_7Cs_{0.01}Si_1$.

The occupying volume, calcining temperature and atomic ratio of alkali metal (Cs) of catalyst (3) were as follows:

occupying volume: 573 mm³ calcining temperature: 500° C.

atomic ratio of Cs: 0.01.

(Oxidation Reaction)

Oxidation reaction of propylene was conducted under identical conditions with those used in Referential Example 1, except that catalyst (3) was used instead of catalyst (1). The results were as shown in Table 1.

Referential Example 4

(Preparation of Catalyst)

Catalyst (4) was prepared in the identical manner with Referential Example 1, except that the amount of cesium nitrate was changed to 2.8 g and the shape of the catalyst was changed to rings of each 9 mm in outer diameter, 2 mm in inner diameter and 9 mm in height. The composition of the alkali metal elements of catalyst (4) was as follows:

$Mo_{12}W_{0.5}Bi_{1.7}Fe_{1.4}Co_7Cs_{0.03}Si_1$.

The occupying volume, calcining temperature and atomic ratio of the alkali metal (Cs) of catalyst (4) were as follows:

occupying volume: 573 mm³ calcining temperature: 480° C.

atomic ratio of Cs: 0.03.

(Oxidation Reaction)

Oxidation reaction of propylene was conducted under identical conditions with those used in Referential Example 1, except that catalyst (4) was used instead of catalyst (1). The results were as shown in Table 1.

Referential Example 5

(Preparation of Catalyst)

Catalyst (5) was prepared in the identical manner with Referential Example 1, except that the amount of cesium nitrate was changed to 4.6 g, and the calcining temperature, to 530° C. The composition of the metal elements of catalyst (5) was as follows:

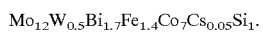

$Mo_{12}W_{0.5}Bi_{1.7}Fe_{1.4}Co_7Cs_{0.05}Si_1.$

The occupying volume, calcining temperature and atomic ratio of alkali metal (Cs) of catalyst (5) were as follows:

occupying volume: 170 mm³ calcining temperature: 530° C.

atomic ratio of Cs: 0.05.

(Oxidation Reaction)

Oxidation reaction of propylene was conducted under identical conditions with those used in Referential Example 1, except that catalyst (5) was used instead of catalyst (1). The results were as shown in Table 1.

Referential Example 6

(Preparation of Catalyst)

Catalyst (6) was prepared in the identical manner with Referential Example 4, except that the shape of the catalyst was changed to rings of each 7 mm in outer diameter, 2 mm in inner diameter and 7.5 mm in height. The composition of the metal elements of catalyst (6) was as follows:

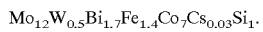

$Mo_{12}W_{0.5}Bi_{1.7}Fe_{1.4}Co_7Cs_{0.03}Si_1.$

The occupying volume, calcining temperature and atomic ratio of alkali metal (Cs) of catalyst (6) were as follows:

occupying volume: 289 mm³ calcining temperature: 480° C.

atomic ratio of Cs: 0.03.

(Oxidation Reaction)

Oxidation reaction of propylene was conducted under identical conditions with those used in Referential Example 4, except that catalyst (6) was used instead of catalyst (4). The results were as shown in Table 1.

Example 1

A stainless steel reactor of 25 mm in diameter was filled with, from the starting gas inlet side toward the outlet side, 500 ml of the catalyst (2) and 1,000 ml of the catalyst (1), by the order stated. A gaseous mixture of 10 volume % of propylene, 16 volume % of oxygen, 10 volume % of steam and 64 volume % of inert gas, whose chief component was nitrogen, was introduced into said reactor with a contact time of 2 seconds and the entrance pressure of 0.2 MPa, and the reaction was continued over 8,000 hours. The performance at the initial period of the reaction and that after the 8,000 hours' operation were as shown in Table 2.

Example 2

The oxidation reaction was carried out in the identical manner with Example 1, except that the catalyst (3) was used instead of the catalyst (2). The results were as shown in Table 2.

Example 3

The oxidation reaction was carried out in the identical manner with Example 1, except that the catalyst (4) was used instead of the catalyst (2). The results were as shown in Table 2.

Comparative Example 1

The oxidation reaction was carried out in the identical manner with Example 1, except that the catalyst (5) was used instead of the catalyst (2). The results were as shown in Table 2.

TABLE 2

| | catalyst | Reaction time (h) | Reaction temp. (° C.) | Hot spot temp. (° C.) | Propylene conversion (mol %) | Selectivity for acrolein + acrylic acid (mol %) | One-pass yield of acrolein + acrylic acid (mol %) |
|---|---|---|---|---|---|---|---|
| Example 1 | (2) + (1) | Initial period | 305 | 378 | 98.1 | 96.2 | 94.4 |
| | | 8,000 | 320 | 385 | 98.3 | 96.5 | 94.9 |
| Example 2 | (3) + (1) | Initial period | 305 | 383 | 98.5 | 95.6 | 94.2 |
| | | 8,000 | 318 | 388 | 98.0 | 95.7 | 93.8 |
| Example 3 | (4) + (1) | Initial period | 305 | 380 | 98.2 | 95.8 | 94.1 |
| | | 8,000 | 320 | 390 | 98.0 | 96.0 | 94.1 |
| Comparative Example 1 | (5) + (1) | Initial period | 307 | 377 | 97.9 | 95.9 | 93.9 |
| | | 8,000 | 345 | 407 | 97.1 | 94.8 | 92.1 |

TABLE 1

| Referential Example | catalyst | Propylene conversion (mol %) | Selectivity for acrolein + acrylic acid (mol %) | One-pass yield of acrolein + acrylic acid (mol %) |
|---|---|---|---|---|
| 1 | (1) | 98.2 | 93.5 | 91.8 |
| 2 | (2) | 82.5 | 96.4 | 79.5 |
| 3 | (3) | 84.1 | 95.8 | 80.6 |
| 4 | (4) | 83.0 | 96.0 | 79.7 |
| 5 | (5) | 81.4 | 96.3 | 78.4 |
| 6 | (6) | 88.4 | 95.4 | 84.3 |

Example 4

A stainless steel reactor of 25 mm in diameter was filled with, from the starting gas inlet side toward the outlet side, 500 ml of the catalyst (2), 500 ml of the catalyst (6) and 500 ml of the catalyst (1) by the order stated. A gaseous mixture of 12 volume % of propylene, 19 volume % of oxygen, 10 volume % of steam and 59 volume % of inert gas, whose chief component was nitrogen, was introduced into said reactor with a contact time of 2 seconds and the entrance pressure of 0.2 MPa, and the reaction was continued over 8,000 hours. The performance at the initial period of the reaction and that after 8,000 hours' operation were as shown in Table 3.

TABLE 3

| | catalyst | Reaction time (h) | Reaction temp. (° C.) | Hot spot temp. (° C.) | Propylene conversion (mol %) | Selectivity for acrolein + acrylic acid (mol %) | One-pass yield of acrolein + acrylic acid (mol %) |
|---|---|---|---|---|---|---|---|
| Example 4 | (2) + (6) + (1) | Initial period 8,000 | 307 322 | 384 391 | 98.0 98.1 | 95.8 96.0 | 93.9 94.2 |

Example 5

The oxidation reaction was carried out in the identical manner with Example 1, except that the starting gas to be introduced into the reactor was changed to a gaseous mixture of 8 volume % of propylene, 14 volume % of oxygen, 10 volume % of steam and 68 volume % of inert gas whose chief component was nitrogen. The results were as shown in Table 4.

TABLE 4

| | catalyst | Reaction time (h) | Reaction temp. (° C.) | Hot spot temp. (° C.) | Propylene conversion (mol %) | Selectivity for acrolein + acrylic acid (mol %) | One-pass yield of acrolein + acrylic acid (mol %) |
|---|---|---|---|---|---|---|---|
| Example 5 | (2) + (1) | Initial period 8,000 | 310 318 | 370 372 | 98.2 98.0 | 96.4 96.5 | 94.7 94.6 |

What is claimed is:

1. A process for producing acrolein and acrylic acid through vapor phase catalytic oxidation of propylene with molecular oxygen or molecular oxygen-containing gas using a fixed bed shell-and-tube reactor, which comprises preparing plural kinds of molded catalysts which are formed of complex oxides of the composition expressed by a general formula (1):

$$Mo_aW_bBi_cFe_dA_eB_fC_gD_hE_iO_x \quad (1)$$

(wherein Mo is molybdenum; W is tungsten; Bi is bismuth; Fe is iron; A is at least an element selected from cobalt and nickel; B is at least an element selected from phosphorus, tellurium, arsenic, boron, antimony, tin, cerium, niobium, lead, chromium, manganese and zinc; C is at least an element selected from alkali metal elements; D is at least an element selected from alkaline earth metal elements; E is at least an element selected from silicon, aluminum, titanium and zirconium; and O is oxygen; a, b, c, d, e, f, g, h, i and x denote the atomic numbers of Mo, W, Bi, Fe, A, B, C, D, E and O, respectively, and where a is 12, b is 0–5, c is 0.1–10, d is 0.1–10, e is 1–20, f is 0–5, g is 0.001–3, h is 0–3, i is 0–30, and x is a numerical value which is determined depending on the extent of oxidation of each of the elements)

and which are different from each other in (α) occupying volume, and (β) calcining temperature and/or (γ) kind and/or amount of the alkali metal element, the molded catalysts which are different from each other in occupying volume (α) being prepared by varying the dimensions of catalyst particles within the range of 3–15 mm, the molded catalysts which are different from each other in calcining temperature being prepared by varying the final calcining temperature (β) within the range of 300–650° C., and the molded catalysts which are different from each other in amount of the alkali metal element (γ) being prepared by varying the atomic number g in the general formula (I) within the range of 0.001–3, and filling the reaction zones provided by dividing the catalyst layer in each of the reaction tubes in the fixed bed shell-and-tube reactor into at least two layers in the axial direction of the tube, sequentially with said plural kinds of molded catalysts in such a manner that the catalytic activity increases from the starting gas inlet side toward the outlet side and the occupying volume decreases from the starting gas inlet side toward the outlet side.

2. A process according to claim 1, in which the number of reaction zones is 2 or 3.

3. A process according to claim 1, in which a starting gas whose propylene concentration is at least 9 volume % is introduced.

4. A process according to claim 2, in which a starting gas whose propylene concentration is at least 9 volume % is introduced.

* * * * *